United States Patent
Satulovsky

(10) Patent No.: US 11,646,185 B2
(45) Date of Patent: May 9, 2023

(54) SYSTEM AND METHOD OF DATA-DEPENDENT ACQUISITION BY MASS SPECTROMETRY

(71) Applicant: Javier E. Satulovsky, Santa Clara, CA (US)

(72) Inventor: Javier E. Satulovsky, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 705 days.

(21) Appl. No.: 16/723,560

(22) Filed: Dec. 20, 2019

(65) Prior Publication Data

US 2020/0144040 A1 May 7, 2020

Related U.S. Application Data

(63) Continuation of application No. 12/785,705, filed on May 24, 2010, now Pat. No. 10,553,412.

(51) Int. Cl.
*H01J 49/00* (2006.01)
*G01N 33/68* (2006.01)

(52) U.S. Cl.
CPC ...... *H01J 49/0031* (2013.01); *G01N 33/6803* (2013.01); *G01N 33/6848* (2013.01); *G01N 33/6878* (2013.01)

(58) Field of Classification Search
CPC ............ H01J 49/0031; G01N 33/6848; G01N 33/6878; G01N 33/6803

USPC .............................. 702/19; 435/7.1; 250/282
See application file for complete search history.

(56) References Cited

U.S. PATENT DOCUMENTS

| | | | |
|---|---|---|---|
| 6,940,065 B2 | 9/2005 | Graber et al. | |
| 7,498,568 B2 | 3/2009 | Overney et al. | |
| 2003/0162221 A1* | 8/2003 | Bader | C12Q 1/485 435/7.1 |
| 2004/0033530 A1* | 2/2004 | Awrey | G01N 33/6851 435/7.1 |
| 2005/0092910 A1* | 5/2005 | Geromanos | H01J 49/0031 435/7.1 |

* cited by examiner

*Primary Examiner* — Kiet T Nguyen

(57) ABSTRACT

Systems, computer-readable media, and methods using mass spectrometry to analyze a sample are provided. For example, a method includes: acquiring a precursor ion spectrum; analyzing the precursor ion spectrum to identify precursor ions that preliminarily match one or more peptides that each belong to at least one protein of interest for the analysis; selecting each of the identified precursor ions in an order according to a ranking protocol for maximizing the number of proteins that are identified in the sample; for each selected precursor ion: acquiring a corresponding product ion spectrum, determining whether the acquired product ion spectrum matches one of the peptides that belong to the set of proteins of interest, and identifying a matched peptide as being present in the sample; and identifying proteins of interest that are present in the sample based on the peptides that are identified as being present in the sample.

20 Claims, 3 Drawing Sheets

SYSTEM AND METHOD OF DATA-DEPENDENT ACQUISITION BY MASS SPECTROMETRY

BACKGROUND

Various analytical instruments can be used for analyzing biological samples to identify peptides, proteins, and other biomolecules that are present in the sample. Mass spectrometry has gained prominence because of its ability to handle a wide variety of biomolecules with high sensitivity and rapid throughput. For example, proteins can be identified via analysis of spectra acquired using a tandem mass spectrometer. In some instances, the proteins are initially digested using a proteolytic agent to produce a variety of peptides, and the peptides are then analyzed by the tandem mass spectrometer to acquire a series of spectra.

In some instances, a tandem mass spectrometer is coupled to a chromatography system to analyze biomolecules present in a sample stream. For example, successive eluting portions of the sample stream can flow from a chromatography column, such as a High Performance Liquid Chromatography ("HPLC") column, into the tandem mass spectrometer, and a series of spectra can be acquired from the eluting portions. While coupling of the tandem mass spectrometer to the chromatography system is desirable for a variety of reasons, such a configuration presents challenges in terms of efficiency at which mass spectrometry data can be acquired during a particular chromatography run. For example, based on analyzing a spectrum acquired from a particular eluting portion of a sample stream, it can be desirable to acquire additional spectra from that same eluting portion. However, the rate of elution of biomolecules present in the sample stream can be too fast for effective manual control of the tandem mass spectrometer. Also, it can be undesirable or impractical to interrupt a flow of the sample stream. In addition, there might be insufficient material for repeated analysis.

Current protocols in tandem mass spectrometry perform a single MS of a sample, and select, among all species observed, a subset of precursor ions for analysis by MS/MS. Both the precursor ions selected for MS/MS, and the parameters used during MS/MS, are selected to maximize the chances of being able to identify the primary sequence—the structure—of the precursor ion. In other words, decisions are made to obtain the highest number of good quality—identifiable—MS/MS spectra. A disadvantage of such an approach is that it does not try to directly increase the protein coverage or sensitivity of the acquisition. For example, an abundant protein whose peptides ionize well, should generate several precursor ions displaying high intensities by MS, and will consume instrument time that could be devoted to inspecting ions of lower intensity that belong to different proteins in the sample.

Consequently, in view of these shortcomings, in some settings a different discovery approach would be desirable.

What is needed, therefore, is a system and method of analyzing biological or chemical samples that can provide improved coverage and sensitivity for detecting specific proteins of interest.

SUMMARY

The present invention provides, inter alia, a method for MS/MS analysis of a sample that contains peptides, when it is known which proteins are of interest. Thus, after the first stage MS analysis, the precursor ions are compared in real time to peptides predicted from the proteins of interest, and only the precursor ions that can potentially belong to a protein of interest will be further analyzed in a next MS stage. In some embodiments, these potential precursor ions are further analyzed in an order according to their priorities, determined based on criteria described herein. As a result, in the limited time allowed for real-time analysis, a maximal number of proteins of interest can be identified.

In an example embodiment, a method is provided for analyzing a sample. The method comprises: (a) providing an inclusion list of proteins of interest in the sample to be analyzed and expected peptides of these proteins, and providing for each peptide in the inclusion list information pertaining to its sequence and at least one property associated with that sequence; (b) performing a mass spectrometry on the sample to acquire a precursor ion spectrum; (c) selecting for further processing a precursor ion whose mass matches a mass of a peptide in the inclusion list which belongs to a protein which has not already been identified in the sample, and for the selected precursor ion: acquiring a product ion spectrum, calculating a match score between the product ion spectrum and one or more peptides in the inclusion list, comparing each match score to a threshold, based on the match score comparisons, determining whether a specific peptide in the inclusion list is present in the sample, and if so, flagging the specific peptide as identified in the sample, and determining whether a protein of interest is identified in the sample based on the extent to which peptides of the protein are identified, and if a protein of interest is identified, then flagging all peptides in the inclusion list that belong to the identified protein as being identified in the sample; and (d) optionally repeating step (c).

In another example embodiment, a method of analyzing a sample comprises: (a) acquiring a precursor ion spectrum for the sample; (b) analyzing the precursor ion spectrum to choose precursor ions whose masses match masses of peptides that belong to one or more proteins of interest for the analysis; (c) among the chosen precursor ions, selecting precursor ions for maximizing a number of proteins that are identified in the sample using a selection criteria that is updated as each new peptide is identified as being present in the sample; (d) for each selected precursor ion, acquiring a corresponding product ion spectrum, determining whether the acquired product ion spectrum matches one of the peptides that belong to the proteins of interest, and identifying a matched peptide as being present in the sample; (e) identifying proteins of interest that are present in the sample based on the peptides that are identified as being present in the sample; and (f) optionally repeating steps (a) to (e).

Other embodiments of the present invention are described elsewhere in this disclosure, including the drawings and claims.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
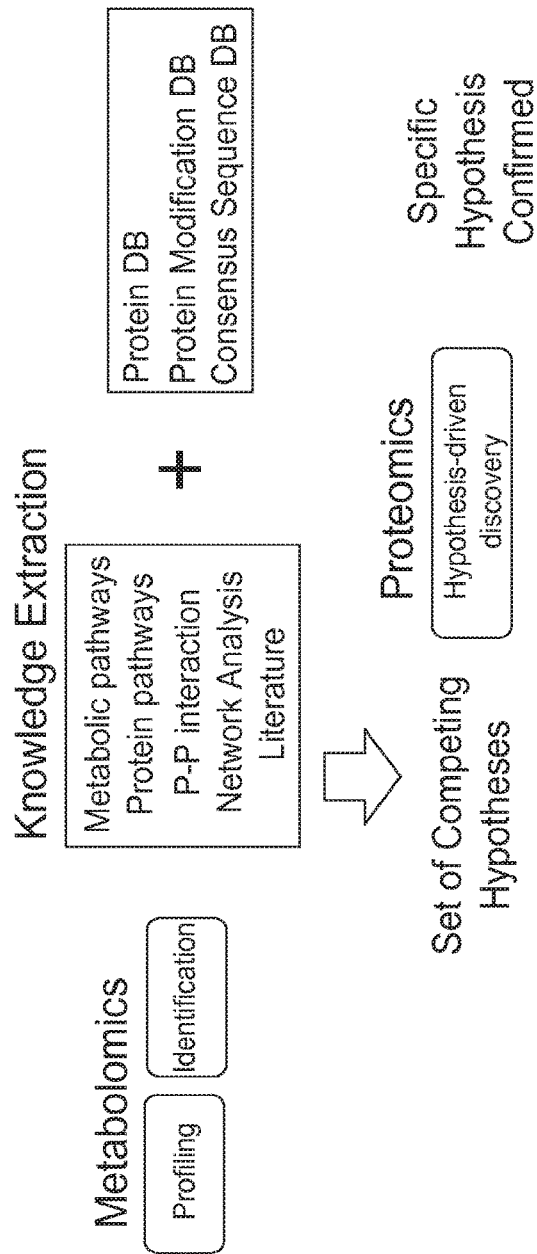
FIG. 1 illustrates a hypothesis-driven protocol for characterizing a biological sample.

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims.

The following definitions apply to some of the elements described with respect to some embodiments of the invention. These definitions may likewise be expanded upon herein.

As used herein, the singular terms "a," "an," and "the" comprise plural referents unless the context clearly dictates otherwise. Thus, for example, reference to a controller can comprise multiple controllers unless the context clearly dictates otherwise.

As used herein, the term "set" refers to a collection of one or more elements. Thus, for example, a set of mass-to-charge ratios can comprise a single mass-to-charge ratio or multiple mass-to-charge ratios. Elements of a set can also be referred to as members of the set. Elements of a set can be the same or different. In some instances, elements of a set can share one or more common characteristics.

As used herein, the term "biomolecules" refers to molecules that can be present in a biological sample. Examples of biomolecules comprise peptides, proteins, oligosaccharides, polysaccharides, lipids, nucleic acids, metabolites, and the like.

As used herein, the term "biological sample" refers to a sample obtained from, derived from, excreted by, or secreted by an organism, such as a unicellular organism or a multicellular organism. Typically, a biological sample comprises a set of biomolecules, such as a set of peptides or a set of proteins. Examples of biological samples comprise blood; plasma; serum; urine; bile; cerebrospinal fluid; aqueous or vitreous humor; bodily secretions; fluids obtained from an abscess or other site of infection or inflammation; fluids obtained from a joint; portions of any tissue or organ; primary cells; cultured cells; and media conditioned by any cell, tissue, or organ. In some instances, biological samples can be subjected to preliminary processing or other sample preparation procedures. For example, biomolecules present in a biological sample can be subjected to cleavage or proteolysis using any of a variety of proteolytic agents, such as trypsin, endoprotease glu-C, cyanogen bromide, and the like. As another example, a biological sample can be subjected to a set of separation procedures, such as subcellular fractionation, one-dimensional electrophoresis, two-dimensional electrophoresis, HPLC, and the like.

As used herein, the term "protein" refers to a molecule comprising multiple amino acids that are linked together. Typically, a protein comprises more than 50 amino acids that are linked together via peptide bonds. Examples of amino acids comprise the 20 genetically encoded amino acids. Additional examples of amino acids comprise D-amino acids, modified amino acids, amino acid analogs, synthetically produced amino acids, and the like. A protein can be naturally occurring, recombinantly produced, or synthetically produced. In some instances, a protein can be subjected to a set of post-translational modifications, such as glycosylation, acetylation, phosphorylation, ubiquitination, and the like.

As used herein, the term "peptide" refers to a molecule comprising multiple amino acids that are linked together. Typically, a peptide comprises multiple amino acids that are linked together via peptide bonds. A peptide can be naturally occurring, recombinantly produced, or synthetically produced. In some instances, a set of peptides can be produced by subjecting a protein to cleavage or proteolysis. A peptide that is produced by cleavage or proteolysis typically comprises from 2 to 50 amino acids, but other lengths are also possible.

As used herein, the term "real-time" refers to performing a set of operations, such that an output or a result of the set of operations is produced based on a particular timing constraint. While an operation is sometimes referred to herein as being performed in real-time, it is contemplated that an output of the operation can be produced with some detectable delay or latency. For example, an operation can be performed in real-time if an output of the operation is produced at a rate that is the same as or substantially the same as a rate at which an input of the operation is acquired. As another example, an operation can be performed in real-time if an output of the operation is produced within a particular upper limit of response time, such as within 1 second, within 0.1 second, within 0.01 second, or within 0.001 second. As a further example, an operation can be performed in real-time if an output of the operation is timely produced so as to be capable of affecting or controlling a process while it is occurring.

In some mass spectrometry scenarios, it would be desirable to have a discovery approach that is not data driven, but hypothesis driven. This desire is a common in basic and clinical research. The goal is to monitor the activity/status of particular protein pathways, protein interaction networks, or sets of proteins defined by a Gene Ontology term, as opposed to finding the most unregulated or downregulated proteins in the sample. In that case, a complete survey of the proteins of interest matters more than how complete the global protein survey of the sample is.

The need for hypothesis driven approach frequently arises as the second iterative cycle in the investigation of the cause of a disease state or the effect of a treatment. In the first phase of an investigation, a global survey of the metabolome, proteome or genome of control and treated/disease samples is performed. By comparing differential change of metabolites, protein or gene expression patterns observed among samples and using curated pathway/protein-protein interaction databases, a researcher creates one or more hypotheses on the mechanistic causes of the phenotypes observed. In the second phase of the investigation these hypotheses are tested. Testing often consists of monitoring the activity of one or more physiological pathways at the protein level. At this point, high protein coverage and sensitivity are critical in order to prove or disprove the hypothesis.

Another scenario where a hypothesis driven proteomics approach would be useful is in drug screening applications. When searching for a drug that affects a particular pathway and not a number of other physiological pathways, one would like to create a long list of multiple reaction monitoring targets that account for all proteins of interest and use a triple quadrupole instrument to screen a large number of drug-treated samples. To optimize the reactions being monitored, however, one would like to start by generating a comprehensive MS/MS spectral dataset of all the proteins in the pathways being monitored. As before, high coverage and sensitivity are important.

As mass spectrometers improve their performance and protein post-translational modifications are better characterized, the hypothesis driven approach becomes more important. In order to understand the role of these protein modifications, the role of the modified protein in regulating physiological pathways needs to be known. For that purpose, accurate snapshots of pathways are needed. These snapshots should be acquired with the raw, highly complex original sample, without pre-processing steps that enrich or reduce the complexity of the sample, since these steps would introduce a strong bias.

FIG. 1 illustrates principles of a hypothesis-driven protocol for characterizing a biological sample. As shown in FIG. 1, metabolomics, including profiling and identification, drives knowledge extraction using network analysis and resources like curated metabolic pathways, protein pathways, protein-protein interactions, and literature. Knowledge extraction produces a set of competing hypotheses. Proteomics employs the hypotheses plus information from existing protein databases, protein modification databases, consensus sequence databases and other relevant databases to perform hypothesis-drive discovery, which ideally confirms a specific hypothesis.

Accordingly, it would be beneficial to use sequence information of a subset of proteins from a database—the proteins of interest—to modify the data-dependent decisions of a tandem mass spectrometer in order to improve the coverage and sensitivity for detecting the specific proteins of interest. More specifically, such data-dependent decisions relate to: (1) how to build an inclusion list for directed tandem mass spectrometry (MS/MS) which uses the sequence of the peptides associated to each protein of interest; (2) how precursor ions are selected for MS/MS scans; and (3) how MS/MS scans are analyzed in real-time to improve the selection of precursor ions for analysis in the remainder of the acquisition.

Toward this end, and as will be described in greater detail below, a method and system is provided for performing a hypothesis driven survey of pathways and protein networks.

Figure 2:
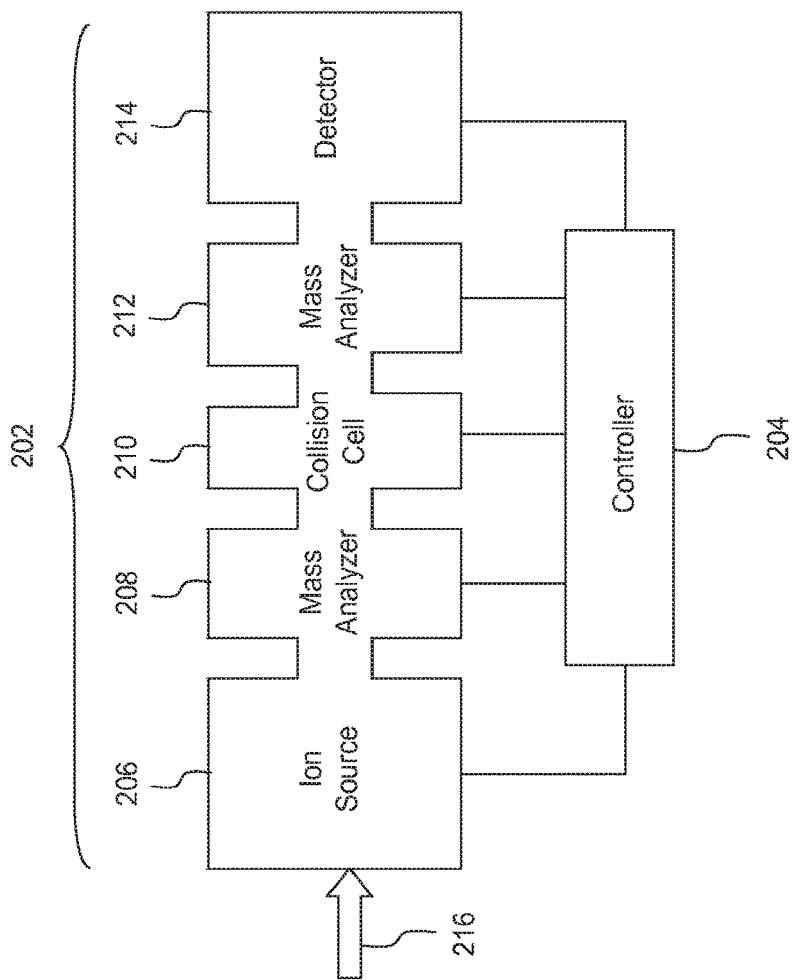
FIG. 2 illustrates an embodiment of a mass spectrometer.

FIG. 2 illustrates an embodiment of a mass spectrometry system 200 that can be employed in a hypothesis driven survey of pathways and protein networks. In particular, in some embodiments mass spectrometry system 200 may execute the method 300 described below with respect to FIG. 3.

Mass spectrometry system 200 comprises a mass spectrometer 202, which is implemented as a tandem mass spectrometer, and a controller 204. In the illustrated embodiment, mass spectrometer 202 can operate in a variety of operational modes, depending on a particular type of mass spectrometry experiment to be conducted. For example, mass spectrometer 202 can operate in a mass spectrometry mode ("MS mode") to acquire a precursor ion spectrum or in a tandem mass spectrometry mode ("MS/MS mode") to acquire a product ion spectrum.

As illustrated in FIG. 2, mass spectrometer 202 comprises an ion source 206, which operates to produce ions. Ions that are produced by ion source 206 serve as precursor ions, which can be fragmented to produce product ions. In one embodiment, ion source 206 may produce ions using Electrospray Ionization ("ESI"). One benefit of ESI is that it can be readily used in conjunction with a variety of separation procedures, such as HPLC. As illustrated in FIG. 2, ion source 206 produces ions from analytes present in a sample stream 216. In particular, sample stream 216 may comprise biomolecules that are dispersed in a suitable solvent. For example, the biomolecules can comprise peptides that are produced by subjecting a set of proteins to cleavage or proteolysis. In one embodiment, sample stream 216 is introduced into ion source 206 in a continuous or flowing fashion from a chromatography column (not illustrated in FIG. 2), such as a HPLC column, and successive eluting portions of sample stream 216 are analyzed by mass spectrometry system 200 as further described below.

Referring to FIG. 2, mass spectrometer 202 is implemented in a tandem-in-space fashion and comprises a pair of mass analyzers 208 and 212 and a collision cell 210, which is positioned between mass analyzers 208 and 212. While two mass analyzers 208 and 212 are illustrated in FIG. 2, it is contemplated that mass spectrometer 202 can comprise more or fewer mass analyzers for other implementations. For example, it is contemplated that mass spectrometer 202 can be implemented in a tandem-in-time fashion, in which case the mass spectrometer 202 can comprise a single mass analyzer. As illustrated in FIG. 2, the mass analyzer 208 is positioned downstream with respect to the ion source 206 to receive ions. Depending on a particular operational mode of mass spectrometer 202, mass analyzer 208 operates to select ions based on mass-to-charge ratio or to transmit all or substantially all ions. Collision cell 210 is positioned downstream with respect to the mass analyzer 208 to receive ions. Depending on a particular operational mode of mass spectrometer 202, collision cell 210 operates to induce fragmentation of ions to produce product ions or to transmit all or substantially all ions. Mass analyzer 212 is positioned downstream with respect to collision cell 210 to receive ions and operates to separate the ions based on mass-to-charge ratio. Mass analyzers 208 and 212 can be implemented in a variety of ways, such as using quadrupole mass analyzers, time-of-flight mass analyzers, ion trap mass analyzers, and the like. Collision cell 210 can be implemented in a variety of ways, such as using an inert gas to induce fragmentation of ions based on dissociation induced by collision.

As illustrated in FIG. 2, mass spectrometer 202 also comprises detector 214, which is positioned downstream with respect to mass analyzer 212 to receive ions. Detector 214 operates to detect the abundance of ions to acquire a set of spectra of sample stream 216. For example, detector 214 can detect the abundance of precursor ions to acquire a precursor ion spectrum or the abundance of product ions to acquire a product ion spectrum. Detector 214 can be implemented in a variety of ways, such as using an electron multiplier, a scintillation counter, and the like.

Referring to FIG. 2, controller 204 is connected to mass spectrometer 202 using any convenient wired or wireless transmission channel and operates to control mass spectrometer 202. In particular, controller 204 directs mass spectrometer 202 to operate in a particular operational mode depending on a particular type of mass spectrometry experiment to be conducted. In conjunction with specifying a particular operational mode, controller 204 can specify or actively change a variety of parameters for mass spectrometer 202, such as parameters for ion source 206, mass analyzers 208 and 212, collision cell 210, and detector 214. For example, controller 204 can specify or actively change ionization settings, ranges of mass-to-charge ratios, spectrum acquisition rates, signal-to-noise ratios, mass resolution, fragmentation settings, detector gain, and the like.

Controller 204 can operate as a real-time engine to perform real-time analysis of acquired spectra and to direct mass spectrometer 202 to operate in a particular operational mode based on results of the real-time analysis. Advantageously, controller 204 allows automated, data-dependent acquisition of mass spectrometry data by specifying or actively changing a type of mass spectrometry experiment to be conducted based on the results of the real-time analysis. In particular, the results of the real-time analysis can be the basis for initiating or refining additional analysis or for initiating or refining acquisition of additional mass spectrometry data. In such manner, controller 204 may improve the efficiency at which mass spectrometry data can be acquired during a particular chromatography run of sample stream 216. Such ability of controller 204 is particularly advantageous in situations where the rate of elution of biomolecules present in sample stream 216 is too fast for effective manual control of mass spectrometer 202, where it is undesirable or impractical to interrupt a flow of sample stream 216, and where there is insufficient material for repeated analysis.

In the illustrated embodiment, controller 204 performs real-time analysis of acquired spectra. For example, during operation of the mass spectrometry system 200, the controller 204 can direct the mass spectrometer 202 to acquire a precursor ion spectrum of a particular eluting portion of the sample stream 216. Next, the controller 204 can perform a real-time analysis of the precursor ion spectrum to identify a set of peaks of interest corresponding to specific precursor ions, and can select one or more of the precursor ions for acquisition of additional mass spectrometry data. In particular, the controller 204 can direct the mass spectrometer 202 to acquire a set of product ion spectra for the selected peaks. By performing the analysis of the precursor ion spectrum in real-time, product ion spectra can be acquired from the same eluting portion of the sample stream 216 from which the precursor ion spectrum was acquired, thus allowing a comprehensive analysis of that eluting portion. The controller 204 can perform a real-time analysis of the product ion spectra to determine whether the set of product ion spectra matches elements of interest.

The controller 204 can be implemented in a variety of ways, such as using computer code, hardwired circuitry, or a combination of computer code and hardwired circuitry. It is contemplated that the controller 204 can comprise or can operate in conjunction with a computing device, such as a personal computer, a server computer, a web appliance, a personal digital assistant product, or the like. For example, in connection with performing analysis of spectra based on a particular evaluation criterion, the controller 204 can operate in conjunction with a search engine residing in a personal computer or in a server computer, which can be connected to the controller 204 using any wired or wireless transmission channel. In some instances, the controller 204 can provide a user interface to allow a user to specify a variety of processing options.

An embodiment of the controller 204 of FIG. 2 relates to a computer storage product with a computer-readable medium comprising computer code or executable instructions thereon for performing a set of computer-implemented operations as described herein, for example a method described and illustrated below with respect to FIG. 3. The medium and computer code can be those specially designed and constructed for the purposes of the invention, or they can be of the kind well known and available to those having ordinary skill in the computer software arts. Examples of computer-readable media comprise: magnetic media such as hard disks, floppy disks, and magnetic tape; optical media such as Compact Disc-Read Only Memories ("CD-ROMs") and holographic devices; magneto-optical media such as floptical disks; and hardware devices that are specially configured to store and execute computer code, such as Application-Specific Integrated Circuits ("ASICs"), Programmable Logic Devices ("PLDs"), and Read Only Memory ("ROM") and Random Access Memory ("RAM") devices. Examples of computer code comprise machine code, such as produced by a compiler, and files comprising higher-level code that are executed by a computer using an interpreter. For example, an embodiment of the invention can be implemented using Java, C++, or other programming language and development tools. Additional examples of computer code comprise encrypted code and compressed code. Moreover, an embodiment of the invention can be downloaded as a computer program product, which can be transferred from a remote computer to a requesting computer by way of data signals embodied in a carrier wave or other propagation medium via a transmission channel. Accordingly, as used herein, a carrier wave can be regarded as a computer-readable medium. Another embodiment of the invention can be implemented in hardwired circuitry in place of, or in combination with, computer code.

Figure 3:
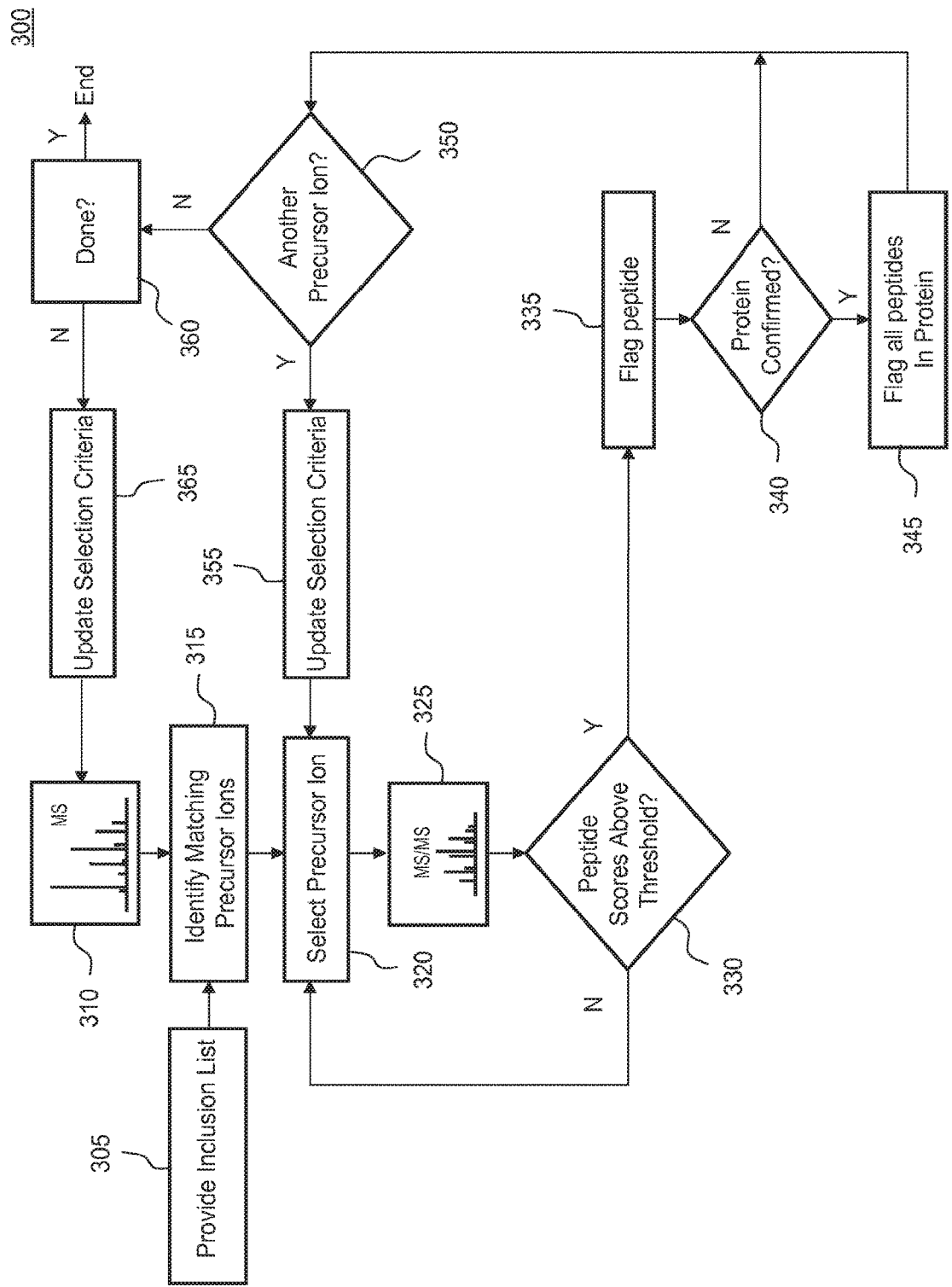
FIG. 3 illustrates one embodiment of a method of processing a biological sample to determine the presence of proteins of interest.

FIG. 3 illustrates one embodiment of a method 300 that can be performed by mass spectrometry system 200 for processing a target sample (e.g., a biological sample) to determine the presence of proteins of interest in the target sample. In particular, FIG. 3 illustrates a process that performs real-time analysis of acquired spectra and directs the mass spectrometer to operate in a particular operational mode based on results of the real-time analysis. In the discussion to follow, an embodiment will be described where method 300 is performed by mass spectrometry system 200. However, it should be understood that in other embodiments, method 300 may be performed by other mass spectrometry systems.

In a step 305 of method 300, an inclusion list of peptides of interest is provided. In some embodiments, peptides in the inclusion list are selected as those peptides that belong to proteins of interest that would be expected to be found in a target sample according to a particular hypothesis that is being tested. In some embodiments, the contents of the inclusion list may include for each peptide of interest information identifying: its mass, one or more of the proteins of interest to which the peptide belongs, the amino acid sequence of the peptide, and properties associated with that sequence, such as predicted or observed chromatographic retention time, predicted or observed proteotypic index for the peptide, and/or other pertinent data. In various embodiments, one or more of these sets of data may be omitted, and/or additional sets of relevant data may be added, like the predicted isotopic envelope of a peptide, intensity of each peptide under a particular fragmentation technique and preferred charge state of a peptide under a particular ionization technique.

According to some embodiments, initially an inclusion list with the sequences of the proteins of interest is digested by computer simulation in order to model the expected digestion and/or additional modifications induced by the sample preparation. The proteins of interest that form the list may be obtained in an automated way from public databases, or may be manually generated. Examples of the number of proteins in typical human pathways are displayed in Table 1 below, which reflects the status of the Kyoto Encyclopedia of Genes and Genomes (KEGG) Pathway databases as of March, 2009.

TABLE 1

| Process | Pathway | Number of Proteins |
| --- | --- | --- |
| Cellular process | MAPK signaling | 270 |
| Cellular process | Regulation of actin cytoskeleton | 216 |
| Cellular process | Focal adhesion | 204 |
| Cellular process | Cell growth and death | 120 |
| Cellular process | T cell receptor signal | 95 |
| Cellular process | Apoptosis | 89 |
| Disease | Colorectal | 84 |
| Disease | Asthma | 30 |
| Cellular process | Folding, sorting and degradation | 23 |

In some embodiments, the inclusion list of protein sequences should contain the unmodified peptides of interest, and any relevant modification of interest of these peptides. If all relevant modifications are not known a priori, they can be predicted based on known consensus sequences for kinases, phosphatases and other enzymes.

Accordingly, controller 204 may be provided with an inclusion list of peptides of interest, each peptide belonging to one or more proteins of interest for the analysis to be performed by mass spectrometry system 200. The inclusion list may be generated by a computer algorithm executed by controller 204 in response to data supplied by a user, for example via a user interface and/or a data input port coupled to controller 204.

Furthermore, as the number of proteins of interests—and peptides in the inclusion list—grows, restrictions on the number of precursor ions selected may be necessary in order to accommodate the time constraints imposed by chromatography. Also, where the inclusion list employs predicted retention times, these times have an intrinsic degree of uncertainty. So as the inclusion list grows, controller 204 may not be able to reliably predict at what time in the precursor ion spectra acquisition process there will be too many precursor ion masses matching the masses of peptides in the inclusion list. However, given that controller 204 has information identifying the sequence of each peptide, in various embodiments one or more of the following techniques may be used to minimize the likelihood of precursor ions being omitted from the MS/MS scans, and, if such omission does happen, to still preserve high protein coverage.

In some embodiments, controller 204 may use the predicted retention time of each peptide of interest to divide the inclusion list into two, or more, smaller inclusion lists, according to the number of mass spectrometry runs that are to be employed in a particular embodiment (that is, each inclusion list is for a different mass spectrometry run, and there are as many runs as there are lists created). Each of these smaller inclusion lists would then include peptides with similar retention times. In some embodiments, peptides with predicted retention times at the end of each time window of a given list also appear in the next inclusion list to account for uncertainty in retention time prediction. In some embodiments, at any given time in the acquisition, the mass-to-charge ratios of precursor ions will be matched against only one of the individual inclusion lists, decreasing the problem of too many precursor ions matching mass-to-charge ratios from the inclusion list.

In some embodiments, controller 204 may decrease the size of the initial inclusion list by removing one or more peptides with the lowest proteotypic index values. Not all peptides have the same likelihood of being detected by mass spectrometry. For instance, peptides may not be observed due to incomplete proteolytic digestion, poor binding or elution from the chromatography column, small size, and/or poor ionization. Classification models exist for determining how likely a particular peptide will be observed in a mass spectrometer. One example is disclosed in W. S. Sanders et al., "Prediction of peptides Observable by Mass Spectrometry Applied at the Experimental Set level," BMC BIOFORMATICS, 8 SUPPL. 7: S23 (2007), the contents of which are hereby incorporated herein by reference in their entirety. Typical peptide features used in the classification models include: number of prolines, percentage of glycine, alanine, leucine, polar amino acids, hydrophobic amino acids and negative amino acids, peptide mass, amphiphilicity index, and propensity to form helices. The proteotypic index of a peptide calculated by these models corresponds to the likelihood of observing that peptide in a mass spectrometry experiment. The proteotypic index may be calculated from the sequence of the peptide or obtained from previously measured values.

Peptides with the lowest proteotypic index values are the least likely to be observed in a mass spectrometry experiment, even when the proteins from which they originate are present. So the decimation of the inclusion list will typically not have a serious adverse effect on coverage and sensitivity at the protein level.

In some embodiments, controller 204 may decrease the size of the initial inclusion list by eliminating redundant peptides. Higher eukaryotes typically have large families of homologous proteins, and it is common for most of the family to participate in the same pathway. In that case, the homology region will carry no information to distinguish one protein from the other. As such, any peptide in the inclusion list whose sequence belongs to more than one protein has no discriminating power. Accordingly, in some embodiments controller 204 removes such peptides from the inclusion list. In some embodiments, in response to user input or under user control, controller 204 may create an exception when information about a post-translationally modified version of a redundant peptide is relevant for a particular study.

Returning again to FIG. 3, in a step 310 a mass spectrometry is performed on the target sample to produce an MS spectrum.

After mass spectrometry system 200 performs an MS scan, in a step 315 the MS spectrum is analyzed, and precursor ions are identified that preliminarily correspond to (e.g., have a same mass) one or more peptides in the inclusion list.

In some embodiments, in step 315 precursor ions are not identified for MS/MS by the expectation that their spectrum can be matched to a peptide, but by whether the masses associated to the peaks in their MS spectrum correspond to one or more masses in the inclusion list of peptides belonging to the proteins of interest. Precursor ions with masses matching the masses of peptides in the inclusion list are identified for subsequent MS/MS scans by mass spectrometry system 200 to acquire corresponding product ion spectra. It should be noted that mass spectrometers do not measure masses directly, but rather measure mass-to-charge ratios. However, from the isotopic envelope of a precursor ion, one can determine the charge of the ion and therefore the mass of the precursor ion. It should also be noted that there may be cases in which the isotopic envelope of a precursor ion is incomplete or distorted, being insufficient to determine precursor mass unequivocally. In these cases, the most common charge states observed in ions in the sample could be considered in the mass match (i.e., multiple matches may be allowed for that precursor ion, all mass matches being equivalent for the purpose of the match).

In a step 320, one of the precursor ions that was identified in step 315 is selected for further processing by tandem mass spectrometry. In some embodiments precursor ions may be selected in step 320 according to a set of rules or criteria to maximize the number of proteins of interest that are detected in the target sample.

In some embodiments, controller 204 selects all of the precursor ions with masses matching the masses of peptides in the inclusion list for subsequent MS/MS scans by mass spectrometry system 200 to acquire corresponding product ion spectra.

By focusing attention on a subset of proteins from a database, mass spectrometry system 200 improves coverage and sensitivity of the proteins of interest. In other words, in some embodiments a precursor ion is not selected for MS/MS by the expectation that its spectrum can be matched to a peptide, but by whether the masses associated with the peaks in its MS spectrum correspond to one or more masses of peptides of the proteins of interest.

While the selection rules described above may resemble the use of a traditional mass inclusion list, further identifications performed on MS/MS spectra as described below render the inclusion list more efficient when dealing with complex samples.

Because of the time constraints, in some cases it may not be possible or practical to perform tandem spectrometry (MS/MS) to acquire product ion spectra for all precursor ions which have masses matching the masses of peptides in the inclusion list. In some embodiments a user of mass spectrometry system 200 may specify a maximum acceptable number of precursor ions to be selected.

In order to match the time constraints of the chromatography, in some embodiments controller 204 may prioritize precursor ions for further MS/MS processing, with a recognition that product ion spectra may not be acquired by MS/MS for those precursor ions having the lowest priority.

In some embodiments, controller 204 may prioritize precursor ions for subsequent MS/MS processing according to one or more of the following criteria.

In some embodiments, controller 204 may prioritize precursor ions for subsequent processing, while still maintaining maximum protein coverage. In that case, for example, in some embodiments controller 204 may assign the lowest priority, or eliminate altogether, precursor ions whose masses matching the masses of peptides from proteins of interest that include peptides that have already been previously identified in the analysis. Here, the goal is to select those precursor ions with the potential to identify the largest number of proteins of interest represented in the inclusion list, as opposed to confirming the presence of proteins which include peptides that have already been identified.

The following two examples illustrate examples of how controller 204 in some embodiments may prioritize precursor ions for further processing, while attempting to preserve maximum protein coverage. In both examples, it is assumed that two precursor ions, A and B, have masses mA and mB matching masses of peptides in the inclusion list.

In the first example, assume that mA matches the mass of a peptide from a protein $P_A$ whose unidentified peptides have very low probability of being observed by mass spectrometry (because they were predicted to elute earlier in the run, or because they have a low proteotypic index). Also assume that the mass match for mB is a peptide from another protein $P_B$ whose yet unidentified peptides have a high probability of existing in the sample (because they are predicted to elute later along the run, or their proteotypic index is high). Assume that the numbers of peptides of both proteins are similar. In that case, in some embodiments the controller 204 may assign higher priority to precursor ion A, because it will increase the chance of identifying protein $P_A$ without a significant detrimental effect on the chance of identifying protein $P_B$.

In the second example, assume that mA matches the mass of a peptide from a large protein that has no previously identified peptides, and mB matches the mass of a peptide from a small protein that has no previously identified peptides, either. Assume that the probability that peptides from each protein exist in the sample is similar. In that case, in some embodiments controller 204 may assign a higher priority to precursor ion B than to precursor ion A for subsequent MS/MS processing, because the likelihood of the large protein being otherwise identified during the rest of the analysis is higher than the likelihood of a small protein being identified during the rest of the analysis.

In some embodiments, a protein coverage maximization approach improves protein sensitivity and reproducibility of protein identifications.

In some embodiments, after the precursor ion elimination or selection criteria disclosed above are applied, controller 204 may further prioritize the precursor ions for further analysis by applying precursor ion elimination or selection rules in order to maximize the likelihood of a match of the MS/MS scan to a peptide in the inclusion list. In some embodiments, these rules may take into account precursor ion intensity, isotopic distribution information, and charge state. For example, in some embodiments, if two precursor ions correspond to the same mass value but have different charge states, controller 204 may select the one with the charge state most likely to yield a good quality MS/MS spectrum. In some embodiments, controller 204 has access to the properties of matching peptides, so selection can be broadened using calculated, theoretically predicted, or previously observed retention times and proteotypic indices of the peptides in the inclusion list.

The following three examples illustrate these principles which may be employed in step 320 for precursor ion selection.

In the first example, assume that the mass mA of precursor ion A matches the mass of a peptide $P_A$ from a first unidentified protein, and that the mass mB of precursor ion B matches the mass of a different peptide, $P_B$, from a second unidentified protein of similar mass to the first unidentified protein. In some embodiments, if the predicted proteotypic index of peptide $P_A$ is greater than the predicted proteotypic index of peptide $P_B$, then controller 204 assigns a higher priority for further MS/MS analysis to precursor ion A than to precursor ion B, since peptide $P_A$ is more likely to exist in the sample than peptide $P_B$ and hence to be identified.

The second example is the same as the first example, but now the calculated retention time of peptide $P_A$ is closer to the actual observed retention time of the precursor ion A than the calculated retention time of peptide $P_B$ is to the actual observed retention time of the precursor ion B. In that case, in some embodiments controller 204 may assign a higher priority to precursor ion A for further MS/MS processing than it assigns to precursor ion B.

The third example is the same as the first example, but now the predicted isotopic envelope of peptide $P_A$ matches the observed isotopic envelope of precursor ion A better than the predicted isotopic envelope of peptide $P_B$ matches the observed isotopic envelope of precursor ion B. In that case, in some embodiments controller 204 may assign a higher priority to precursor ion A for further MS/MS processing than it assigns to precursor ion B.

In various embodiments, any or all of the precursor prioritization, or elimination, criteria described above may be employed in step 320 of method 300.

In a step 325, a product ion spectrum is obtained for the selected precursor ion via tandem mass spectrometry.

In a step 330, it is determined whether the product ion spectrum matches one of the peptides in the inclusion list to a sufficient degree that a decision should be made that the precursor ion corresponds to that peptide. In some embodiments, step 330 may include calculating a match score and comparing it to a threshold.

In some embodiments, once the MS/MS scan of a selected precursor ion is acquired in step 225, controller 204 calculates a spectrum-to-peptide match score based on the peptide sequences in the inclusion list. Alternatively, controller 204 may calculate spectrum-to-spectrum scores from a spectral database of the peptides in the inclusion list. Other methodologies for calculating a peptide match score may be employed. Given knowledge of the sequence of the peptide in question and knowledge of what peptides have been previously acquired, in some embodiments controller 204 can make the score threshold peptide-specific to reduce the rate of false positive and false negative identifications. For example, in some embodiments, given a base score threshold value, controller 204 may obtain a more accurate peptide-specific threshold by one or more of the techniques described below.

In some embodiments, retention times for peptides in the inclusion list may be predicted using models such as the Sequence Specific Retention Calculator disclosed by O. V. Krokhin et al., "An Improved Model for Prediction of Retention Times of Tryptic Peptides on Ion Pair Reversed-phase HPLC: Its Application to Protein Peptide Mapping by Off-Line HPLC-MALDI MS," MOL. CELL PROTEOMICS, 3(9), pp. 908-919 (2004), the contents of which are hereby incorporated herein by reference in their entirety. In the Sequence Specific Retention Calculator model, properties like the retention coefficient assigned to each amino-acid, nearest neighbors effects, clusters of hydrophobic amino acids, proline content, isoelectric point of the peptide, peptide length, and propensity for helical structure, are taken into account to estimate the predicted elution time of the peptide.

In some embodiments, controller 204 may decrease the scoring threshold for a particular peptide if the actual observed retention time of the precursor ion matches, within a specified error, the predicted retention time of the peptide in the inclusion list. Similarly, controller 204 may increase the scoring threshold for a particular peptide as the difference between the actual observed retention time of the precursor ion, and the predicted retention time of the peptide, increases.

In some embodiments, controller 204 may decrease the scoring threshold for a particular peptide if the peptide being matched has a high proteotypic index. Similarly, controller 204 may increase the score threshold for a specific peptide that has a low proteotypic index, given that, normally, one would not expect to detect that peptide in the experiment.

Identifying one or more peptides from a protein increases the likelihood that other peptides of the same protein are present in the sample and hence will be detected. For example, assume that two peptides of a given protein have been identified and a new precursor ion matches a mass-to-charge ratio corresponding to a third, yet unidentified, peptide of the same protein. In that case, in some embodiments controller 204 may decrease the score threshold for that peptide based on the increased likelihood of the existence of that peptide in the sample. As a variant of the approached just described, in some embodiments controller 204 may compare the precursor ion intensity of previously identified peptides with the intensity of the peptide being analyzed, and the strength of the correlation between them predicted from the peptide and the correlation between them observed could be used to further decrease the score threshold for the peptide being analyzed.

As the number of pathways—and proteins being monitored—grows, the mass of a precursor ion may match the mass of more than one peptide in the inclusion list. In that case, in some embodiments controller 204 may calculate a spectrum-to-peptide match score for each of the matching target peptides in the inclusion list, and compare each spectrum-to-peptide match score to the score threshold for that peptide. If none of the match scores qualify (is above its threshold) then controller 204 may determine that the identification is inconclusive, and no further action is taken for that product ion spectrum, i.e. process returns to step 220 and the next precursor ion is scanned by MS/MS. If only one of the scores qualifies, controller 204 may consider the peptide to be a bona fide identification and may flag that peptide in the inclusion list as being identified in the sample, in which case it may be removed from future searches. If more than one score for more than one peptide qualifies, however, controller 204 may employ different strategies depending on how aggressive or conservative the identification is desired to be. In one strategy, controller 204 may determine that only the peptide with the highest score among qualifying peptides is considered is a correct identification, and is flagged in the inclusion list as identified. In another strategy, controller 204 may consider the analysis to be inconclusive and no further action is taken (i.e. the next precursor ion is scanned by MS/MS).

Whatever the methodology that is employed, in step 330 controller 204 compares a match score from the product ion spectrum produced in step 325 to a suitable score threshold, and as a result of the comparison a decision is made on whether the product ion spectrum matches a peptide or not. If no peptide in the inclusion list is identified as corresponding to the product ion spectrum, then the process returns to step 320 where another precursor ion is selected for further processing.

On the other hand, when the match between the product ion spectrum and a peptide of interest is high enough, in a step 335 controller 204 may flag that peptide as having been identified or present in the sample, and the peptide may be effectively excluded from further searches by mass spectrometry system 200.

Assuming that other peptides in the inclusion list do not have the same mass-to-charge ratio as the peptide in question, then in some embodiments no further precursor ions having that mass-to-charge ratio may be selected by controller 204 for MS/MS by mass spectrometry system 200, making the acquisition more efficient, especially when working with complex samples.

By using sequence information to confirm, in real time, the identity of the precursor ions, controller 204 can also identify, in real time, which of the proteins of interest are present in the sample. This can be achieved, for example, by counting a minimum number of peptides of a given protein that have been confidently identified.

Accordingly, in a next step 340 it is determined whether or not the identification of the newly identified peptide results in a confirmation that a newly identified protein is present in the target sample. This may be done, by example, by controller 304 comparing the number (or percentage) of peptides that have been identified and that belong to a particular protein to a threshold, and once the threshold is reached, making a decision that the protein is present in the target sample.

If no new protein is confirmed to be present in the sample as a result of the new peptide that was identified in step 330 and flagged in step 335, then the process proceeds to step 350 which will be described below.

On the other hand, if, as a result of a new peptide being identified and flagged in steps 340 and 345, controller 204 confirms that enough peptides belonging to a particular protein have been confirmed as being present in a sample that is being analyzed, then controller 204 determines that the protein itself is present in the sample being analyzed and method 200 proceeds to step 345.

In step 345 all the remaining peptides in the inclusion list that belong to the newly identified protein from step 340 are flagged as having been identified in the target sample, and are thereby effectively removed from further searches in subsequent processing and analysis steps of the method. In some embodiments, this may increase protein coverage and sensitivity, since it will focus instrument time into analyzing precursor ions of peptides from different proteins of interest that have not already been identified.

In some embodiments, controller 204 may provide an exception for peptides having modifications. In some embodiments, peptide modifications are considered as separate peptide entries in the inclusion list, in which case both the modified and unmodified entries may be retained. The effect of dynamically reducing the number of the peptides to be searched as a result of protein identification can make the acquisition more efficient as the analysis proceeds along, since there will be progressively fewer precursor ions whose mass matches masses of peptides from the inclusion list.

In step 350 it is determined whether or not another precursor ion is to be analyzed for the current MS spectrum. For example, a user may set a limit of the number of precursor ions (e.g., five or six) to be analyzed via MS/MS for each MS spectrum. Or there may be a limit on the amount of time that may be taken for analyzing each MS spectrum that is obtained from a sample.

If it is determined in step 350 that another precursor ion is to be analyzed, then the process proceeds to step 355.

In step 355, the selection criteria that are employed in step 320 for selection of a next precursor ion for analysis, examples of which are discussed in detail above, are updated as appropriate based on the identification of a new peptide and/or protein in the target sample in steps 330 and/or step 340. Then the process repeats at step 320.

On the other hand, if it is determined in step 350 that no more precursor ions are to be analyzed for this MS spectrum, then the process proceeds to step 360 where it is determined if the sample analysis is complete. If so, then the process ends. Otherwise, in step 365 the selection criteria are updated as appropriate based on the identification of a new peptide and/or protein in the target sample in steps 330 and/or step 340. Then the process repeats with a new mass spectrometry at step 310.

It should be understood that the order of some of the various steps in method 300 may be rearranged. For example, in some embodiments the selection criteria may be updated before step 350 where it is determined if another precursor ion is to be analyzed.

In some embodiments, when mass spectrometry system 200 is analyzing a treated sample against a control sample, the following procedure may be employed. First, the control sample is run in a tandem mass spectrometer as described above. Then, from the inclusion list used in the control sample, controller 204 may produce a match list comprising the subset of peptides flagged as identified or confirmed in the control sample. Next, the match list obtained from the control sample may be used as the inclusion list for analyzing the treated sample, and an analysis may be performed on the treated sample, as described above. In this case, for example, the inclusion list for the treated sample will include the observed—not predicted—retention times of each precursor, and these observed retention times are employed for each precursor ion to select precursor ions for MS/MS analysis.

While example embodiments are disclosed herein, one of ordinary skill in the art appreciates that many variations that are in accordance with the present teachings are possible and remain within the scope of the appended claims. The invention therefore is not to be restricted except within the scope of the appended claims.

The invention claimed is:

1. A method of analyzing a sample with tandem mass spectrometry, comprising:
   (a) providing an inclusion list of proteins of interest and expected peptides of the proteins of interest, and providing for each peptide in the inclusion list information pertaining to the peptide's sequence and at least one property associated with the peptide's sequence;
   (b) performing mass spectrometry on the sample to acquire a precursor ion spectrum;
   (c) selecting for further processing a precursor ion whose mass matches the mass of a peptide in the inclusion list which belongs to a protein which has not already been identified in the sample, and for the selected precursor ion:
   acquiring a product ion spectrum,
   calculating a match score between the product ion spectrum and one or more peptides in the inclusion list,
   comparing each match score to a threshold,
   based on the match score comparisons, determining whether a specific peptide in the inclusion list is present in the sample, and if so, flagging the specific peptide as identified in the sample, and
   determining whether a protein of interest is identified in the sample based on the extent to which peptides of the protein are identified, and if a protein of interest is identified, then flagging all peptides in the inclusion list that belong to the identified protein as being identified in the sample; and
   (d) repeating step (c).

2. The method of claim 1, further comprising repeating steps (b) through (d).

3. The method of claim 1, wherein the calculating a match score and comparing each match score comprise comparing an observed retention time of the precursor ion with a predicted retention time of each of the one or more peptides.

4. The method of claim 1, wherein the calculating a match score and comparing each match score comprise adjusting at least one of the match score and the threshold for at least one peptide based on a proteotypic index of the one peptide.

5. The method of claim 1, wherein the calculating a match score and comparing each match score comprise adjusting at least one of the match score and the threshold for at least one peptide if other peptides have been identified for the protein of interest said one peptide belongs to.

6. The method of claim 1, wherein when the match scores for two or more of the peptides exceed the threshold, and one of the match scores is highest, determining the peptide having the highest match score as present in the sample.

7. The method of claim 1, wherein the selecting for further processing comprises:
ranking for subsequent processing the precursor ions whose masses match masses of peptides in the inclusion list in an order based at least in part on maximizing the number of the proteins of interest identified by the analysis; and
selecting and processing the precursor ions in said order.

8. The method of claim 7, wherein the ranking comprises assigning a higher priority to precursor ions whose masses only match masses of peptides belonging to proteins of interest with unidentified peptides that have low likelihood of being identified based on their predicted and/or observed retention time and proteotypic index, and assigning a lower priority to precursor ions whose masses only match masses of peptides belonging to proteins of interest with unidentified peptides that have high likelihood of being identified based on their predicted or observed retention time and/or proteotypic index.

9. The method of claim 7, wherein the ranking comprises assigning a higher priority to precursor ions whose masses only match masses of peptides belonging to proteins of interest expected to have smaller number of peptides, and assigning a lower priority to precursor ions whose masses only match masses of peptides belonging to proteins of interest expected to have a large number of peptides.

10. The method of claim 7, wherein the ranking comprises ranking the precursor ions based at least in part on one or more of the following criteria: (1) a proteotypic index for a peptide whose mass matches the precursor ion mass; (2) the difference between an observed retention time of the precursor ion and a predicted retention time for a peptide whose mass matches the precursor ion mass; and (3) a match between an observed isotopic envelope of the precursor ion and a predicted isotopic envelope of a peptide whose mass matches the precursor ion mass.

11. The method of claim 1, wherein the selecting for further processing comprises selecting those precursor ions whose masses match peptides having a highest proteotypic index among those peptides whose masses match one or more of the precursor ions.

12. The method of claim 1, wherein the selecting for further processing comprises selecting precursor ions whose masses match a peptide that only belong to one of the proteins of interest.

13. A computer-readable medium comprising codes for executing the method of claim 1.

14. A mass spectrometry system comprising:
a mass spectrometer; and
a controller connected to the mass spectrometer, the controller including a processor configured to execute the method of claim 1.

15. The system of claim 14, wherein the controller is configured to provide the inclusion list in response to data supplied by a user of the system.

16. The system of claim 14, wherein the controller is configured to select for further processing precursor ions whose masses match masses of peptides in the inclusion list, by:
ranking the precursor ions whose masses match masses of peptides in the inclusion list in an order for subsequent processing based at least in part on maximizing the number of the proteins of interest identified by the analysis; and
selecting and processing the precursor ions in said order.

17. The system of claim 16, wherein the controller is configured to rank the precursor ions in part based on one or more of the following criteria: (1) the size of the protein of interest to which a peptide matched to the precursor ion belongs; (2); a proteotypic index of a peptide matched to the precursor ion; (3) the difference between an observed retention time and a predicted retention time of a peptide matched to the precursor ion; and (4) a match between an observed isotopic envelope of the precursor ion and a predicted isotopic envelope of a peptide matched to the precursor ion.

18. A method of analyzing a sample by tandem mass spectrometry, comprising:
(a) acquiring a precursor ion spectrum for the sample;
(b) analyzing the precursor ion spectrum to choose precursor ions whose masses match masses of peptides that belong to one or more proteins of interest for the analysis;
(c) among the chosen precursor ions, selecting precursor ions for maximizing a number of proteins that are identified in the sample using a selection criterion that is updated as each new peptide is identified as being present in the sample;
(d) for each selected precursor ion,
acquiring a corresponding product ion spectrum,
determining whether the acquired product ion spectrum matches one of the peptides that belong to the proteins of interest, and
identifying a matched peptide as being present in the sample;
(e) identifying proteins of interest that are present in the sample based on the peptides that are identified as being present in the sample; and
(f) repeating steps (a) to (e).

19. The method of claim 18, wherein said analyzing the precursor ion spectrum comprises:
providing an inclusion list of peptides of interest, each peptide belonging to one of the proteins of interest, the inclusion list comprising for each peptide of interest at least one of the following: (1) a predicted retention time for the peptide, (2) at least one of the proteins of interest to which the peptide belongs, and (3) a sequence of the peptide; and
comparing the mass of the precursor ion to masses of the peptides in the inclusion list.

20. The method of claim 18, wherein the selection criterion comprises one or more of the following criteria: (1) the size of the protein of interest to which a peptide matched to the precursor ion belongs; (2); a proteotypic index of a peptide matched to the precursor ion; (3) the difference between an observed retention time and a predicted retention time of a peptide matched to the precursor ion; and (4) a match between an observed isotopic envelope of the precursor ion and a predicted isotopic envelope of a peptide matched to the precursor ion.

* * * * *